(12) United States Patent
Chen et al.

(10) Patent No.: US 12,004,748 B2
(45) Date of Patent: Jun. 11, 2024

(54) CIRCULAR STAPLER WITH AUDIBLE INDICATOR

(71) Applicant: TOUCHSTONE INTERNATIONAL MEDICAL SCIENCE CO., LTD., Jiangsu (CN)

(72) Inventors: Zhi Chen, Jiangsu (CN); Yi Guo, Jiangsu (CN); Jiang Lin, Jiangsu (CN)

(73) Assignee: Touchstone International Medical Science Co., Ltd., Jiangsu (CN)

( * ) Notice: Subject to any disclaimer, the term of this patent is extended or adjusted under 35 U.S.C. 154(b) by 181 days.

(21) Appl. No.: 17/311,206

(22) PCT Filed: Dec. 20, 2019

(86) PCT No.: PCT/CN2019/126923
§ 371 (c)(1),
(2) Date: Jun. 4, 2021

(87) PCT Pub. No.: WO2020/125746
PCT Pub. Date: Jun. 25, 2020

(65) Prior Publication Data
US 2022/0031329 A1    Feb. 3, 2022

(30) Foreign Application Priority Data

Dec. 20, 2018   (CN) .......................... 201811564095.4
Dec. 20, 2018   (CN) .......................... 201822145985.3

(51) Int. Cl.
*A61B 17/068* (2006.01)
*A61B 17/11* (2006.01)
(Continued)

(52) U.S. Cl.
CPC ....... *A61B 17/1155* (2013.01); *A61B 17/1114* (2013.01); *A61B 17/326* (2013.01);
(Continued)

(58) Field of Classification Search
CPC ........ A61B 17/1155; A61B 2090/0807; A61B 17/068; A61B 2017/00115
See application file for complete search history.

(56) References Cited

U.S. PATENT DOCUMENTS 5,685,474 A    11/1997   Seeber
7,967,178 B2 *  6/2011   Scirica ............. A61B 17/07207
                                                          227/19
(Continued)

FOREIGN PATENT DOCUMENTS

CN    1736339 A    2/2006
CN    1973782 A    6/2007
(Continued)

OTHER PUBLICATIONS

First Office Action regarding corresponding RU App. No. 2021117990/14; dated Jan. 21, 2022.
(Continued)

*Primary Examiner* — Gloria R Weeks
(74) *Attorney, Agent, or Firm* — Dickinson Wright PLLC

(57) ABSTRACT

The present disclosure provides a circular stapler including an instrument body, a handle assembly and a staple pushing rod; wherein an indicator and a strike part are disposed in the instrument body, and the indicator is rotatably connected to the instrument body; when the stapler is in an initial state, the indicator is in a first position area and pressed against the strike part; when the stapler is in a firing state, the indicator is moved to a second position area and separated from the strike part; when the stapler being fired, the indicator returns to the first position area from the second position area, strikes the strike part and emits a strike sound. The strike sound prompts an operator that firing has been successfully (Continued)

completed, so that the operator can know the firing state of the stapler in time and user experience of the operator can be improved.

17 Claims, 21 Drawing Sheets

(51) Int. Cl.
    *A61B 17/115*     (2006.01)
    *A61B 17/326*     (2006.01)
    *A61B 90/00*     (2016.01)
    *A61B 17/00*     (2006.01)

(52) U.S. Cl.
    CPC .............. *A61B 90/03* (2016.02); *A61B 90/08* (2016.02); *A61B 2017/00119* (2013.01); *A61B 2017/1132* (2013.01); *A61B 2017/1135* (2013.01); *A61B 2090/033* (2016.02); *A61B 2090/0807* (2016.02)

(56) References Cited

U.S. PATENT DOCUMENTS

| | | | |
|---|---|---|---|
| 8,033,438 B2 * | 10/2011 | Scirica | A61B 17/07207 |
| | | | 227/176.1 |
| 10,932,845 B2 * | 3/2021 | Worrell | A61B 18/1445 |
| 2010/0108741 A1 | 5/2010 | Hessler et al. | |
| 2016/0374681 A1 | 12/2016 | Miller et al. | |
| 2017/0181748 A1 | 6/2017 | Hessler et al. | |
| 2017/0348002 A1 * | 12/2017 | Murugesan | A61B 17/07207 |
| 2018/0296219 A1 * | 10/2018 | Zhang | A61B 17/1155 |

FOREIGN PATENT DOCUMENTS

| | | |
|---|---|---|
| CN | 1989912 A | 7/2007 |
| CN | 102641146 A | 8/2012 |
| CN | 103142274 A | 6/2013 |
| CN | 204092080 U | 1/2015 |
| CN | 204410896 U | 6/2015 |
| CN | 109953795 A | 7/2019 |
| CN | 209529239 U | 10/2019 |
| EP | 2800525 A1 | 11/2014 |
| EP | 3123954 A2 | 2/2017 |
| JP | 2018521791 A | 8/2018 |
| WO | 2010048811 A1 | 5/2010 |
| WO | 2015139137 A1 | 9/2015 |
| WO | 2015139197 A1 | 9/2015 |
| WO | 2017079970 A1 | 5/2017 |
| WO | 2018161314 A1 | 9/2018 |
| WO | WO 2018/161314 * | 9/2018 ........... A61B 17/115 |

OTHER PUBLICATIONS

Extended European Search Report regarding corresponding EP App. No. 19900362.5; dated Jan. 11, 2022.
English translation of First Office Action regarding corresponding JP App. No. 2021-535924; dated May 31, 2022.
First Office Action regarding corresponding CN App. No. 201811564095.4; dated Apr. 7, 2023 ..
Notice of Allowance dated Sep. 26, 2023 for Korean Application No. 10-2021-7019900.

* cited by examiner

CIRCULAR STAPLER WITH AUDIBLE INDICATOR

CROSS-REFERENCE TO RELATED APPLICATIONS

This application is based upon PCT patent application No. PCT/CN2019/126923, filed on Dec. 20, 2019, which claims priority to Chinese Patent Application No. 201822145985.3 filed on Dec. 20, 2018, and Chinese Patent Application No. 201811564095.4, filed on Dec. 20, 2018, the entire contents of which are incorporated herein by reference.

TECHNICAL FIELD

The present disclosure relates to the field of medical instrument technology, in particular to a circular stapler.

BACKGROUND

Digestive tract disease is one of human diseases of high incidence. During treatment, a circular stapler is widely used for suturing physiological tissues such as tissues in the digestive tract, instead of the manual operation by doctors. The circular stapler is a common surgical instrument, and used for end-to-end anastomosis, or end-to-side anastomosis of the physiological tissues of esophagus, stomach, intestine, etc., in a way of axial internal stapling. During the process of anastomoses, two sections of tissues are accommodated in the circular stapler, and form a circular anastomotic stoma after firing the circular stapler, to rebuild a tissue channel.

In the prior art, the circular stapler includes an instrument body, a handle assembly movably connected to the instrument body and an anvil assembly cooperated with the instrument body. The instrument body includes a cartridge assembly located at a distal end and a knob located at a proximal end thereof. The cartridge assembly includes a circular cartridge and a cutter, and the knob can be rotated relative to the instrument body. The instrument body further includes an anvil shaft disposed inside thereof, from the proximal end to the distal end. In the present disclosure, positions of the distal end and the proximal end are defined relative to an operator, wherein, the proximal end is an end closer to the operator, and the distal end is another end far from the operator and closer to a surgical position. Further, in the circular stapler, inside and outside are defined relative to an axis of the circular stapler, wherein, the inside is a side closer to the axis, and the outside is another side far from the axis. The anvil assembly includes an anvil, an anvil cap disposed on a distal end of the anvil and a cutter anvil disposed inside the anvil. The anvil assembly can be connected, directly to a distal end of the anvil shaft, or by an anvil shaft connector. During tumor operation, after tumor tissues are separated and removed, the anvil shaft is connected to the distal end of the instrument body through a purse at one end of the tissues, the knob is rotated to drive the anvil assembly to move close to the cartridge. The circular stapler is then able to be fired by pressing the handle assembly to accomplish the suturing operation. Along with the development of medical instruments, the circular stapler has been more and more widely used for treatment of diseases such as hemorrhoids.

Meanwhile, in urinary surgical field, another kind of circular stapler is also applied to treat redundant prepuce and phimosis, which is called circumcision stapler. Structure of the circumcision stapler is similar to the circular stapler for digestive tract as aforementioned, except for a glans cap assembly cooperated with the instrument body. Similarly, the glans cap assembly includes an anvil, a glans cap fixedly connected to the anvil, a cutter anvil and a central rod detachably connected to the instrument body. During operation, prepuce tissues to be cut are fixed to the glans cap, the central rod is configured to the distal end of the instrument body, and the knob is rotated to shorten a distance between the glans gap and the circular cartridge to an appropriate distance. The circular stapler is then able to be fired by pressing the handle assembly to accomplish the suturing operation.

However, during the process of operation, the doctor usually cannot visually observe the firing state of the circular stapler after pressing the handle assembly, nor can he feel whether the firing is completed through sense of touch, which results poor user experience of the doctor.

SUMMARY

In view of the problems in the prior art, a purpose of the present disclosure is to provide a circular stapler. When the firing of the stapler is completed, a first end of an indicator returns to a first position area from a second position area, strikes a strike part and emits a strike sound, thereby prompting the operator that the firing has been successfully completed through the strike sound.

Embodiments of the present disclosure provide a circular stapler including: an instrument body, wherein an indicator and a strike part are disposed in the instrument body, and the indicator is rotatably connected to the instrument body; a handle assembly movably connected to the instrument body; and a staple pushing rod disposed in the instrument body, wherein the staple pushing rod has an initial position and a firing position, and the staple pushing rod is capable of being pushed to the firing position, by the handle assembly, from the initial position; when the circular stapler is in an initial state, a first end of the indicator is in a first position area and located correspondingly to the strike part; when the circular stapler is in a firing state, the first end of the indicator is moved to a second position area and away from the strike part; after the circular stapler being fired, the first end of the indicator returns to the first position area from the second position area, strikes the strike part and emits a strike sound.

In some embodiments, an elastic limiting member is disposed in the instrument body, and a free end of the elastic limiting member is oriented toward and held against the first end of the indicator, when located in the first position area, the first end of the indicator is not held against the strike part.

In some embodiments, the elastic limiting member is a spring.

In some embodiments, the first end of the indicator is connected to a distal end of a pulling sheet, and driven by the pulling sheet, the first end of the indicator is capable of being moved to the second position area from the first position area.

In some embodiments, the instrument body includes two stapler casings disposed on both sides of the circular stapler, respectively, a first end and a second end of the strike part are respectively fixed to inner surfaces of the two stapler casings, and a middle portion of the strike part is protruded toward a proximal direction of the circular stapler.

In some embodiments, a rib plate and a fixing plate are disposed on the inner surface of each of the stapler casings, and a fixing slot is formed between the rib plate and the fixing plate, both ends of the strike part are respectively inserted into two fixing slots.

In some embodiments, the strike part is a metal sheet with a middle portion bent toward a proximal direction of the circular stapler.

In some embodiments, the strike part is a hollow sphere or a hemisphere with a spherical surface facing a proximal direction of the circular stapler.

In some embodiments, the strike part includes a bell and a bracket, and the bell is fixed to the instrument body through the bracket.

In some embodiments, the instrument body includes two stapler casings disposed on two sides of the instrument body, respectively, and two ends of the bracket are respectively fixed to the stapler casings on the two sides.

In some embodiments, an inner surface of each of the stapler casings is provided with a slot, and the two ends of the bracket are respectively inserted into slots on the two sides.

In some embodiments, the bell is a hollow cylinder with an opening on a bottom surface, and the bracket comprises a connecting part and a first side arm and a second side arm disposed on both sides of the connecting part, the connecting part of the bracket is fixedly connected to a middle portion of an upper surface of the bell, and terminal ends of the first side arm and the second side arm of the bracket are respectively fixed to the stapler casings on the two sides.

In some embodiments, the indicator further includes a positioning part, and the indicator is rotatably fixed to the instrument body through the positioning part.

In some embodiments, a firing part protruding toward a distal end of the circular stapler is disposed on the first end of the indicator, after the stapler being fired, the indicator returns to the first position area from the second position area, and the firing part of the indicator strikes the strike part and emits the strike sound.

In some embodiments, the circular stapler further comprises a positioning pin passing through the positioning part, and an indicator return torsion spring is sleeved on the positioning pin.

In some embodiments, the instrument body includes two stapler casings disposed on two sides of the instrument body, respectively, the positioning part is fixed to the stapler casing on one side, and the first end of the indicator includes an indicating part protruding toward the stapler casing on the other side.

In some embodiments, the instrument body includes a stapler casing, and at least one sound hole is opened at a position, of the stapler casing, corresponding to the strike part.

The circular stapler provided by the present disclosure has following advantages.

The present disclosure provides a circular stapler with the strike part disposed inside the instrument body. When firing the stapler, the first end of the indicator is moved to the second position area from the first position area and away from the strike part; when the firing is completed, the first end of the indicator returns to the first position area from the second position area, strikes the strike part and emits the strike sound. The strike sound prompts an operator that the firing has been successfully completed, so that the operator can know the firing state of the circular stapler in time and user experience of the operator can be improved.

BRIEF DESCRIPTION OF THE DRAWINGS

In order to describe technical solutions in the embodiments of the present disclosure more clearly, the following will briefly introduce accompanying drawings used in description of the embodiments. Obviously, the accompanying drawings in the following description show only some embodiments of the present disclosure. For those of ordinary skill in the art, other drawings can be obtained on the basis of these drawings without creative work.

DETAILED DESCRIPTION

In order to make the objectives, technical solutions, and advantages of embodiments of the present disclosure clearer, the technical solutions in the embodiments of the present disclosure will be described clearly and completely in conjunction with accompanying drawings. Obviously, the embodiments described are only part and not all of the embodiments of the present disclosure.

Hereinafter, the present disclosure will be described in detail with reference to the drawings and in conjunction with the embodiments.

In order to solve the technical problems in the prior art, the present disclosure provides a circular stapler including an instrument body, a handle assembly movably connected to the instrument body and a staple pushing rod disposed in the instrument body, the staple pushing rod has an initial position and a firing position, and the staple pushing rod can be pushed to the firing position, by the handle assembly, from the initial position; further an indicator and a strike part are disposed in the instrument body, and the indicator is rotatably connected to the instrument body.

When the circular stapler is in an initial state, a first end of the indicator is in a first position area and located correspondingly to the strike part; when the circular stapler is in a firing state, the first end of the indicator is moved to a second position area and away from the strike part; after the circular stapler being fired, the first end of the indicator returns to the first position area from the second position area, strikes the strike part and emits a strike sound. The strike sound prompts an operator that the firing has been successfully completed, so that the operator can know the firing state of the circular stapler in time, and user experience of the operator can be improved.

Figure 1:
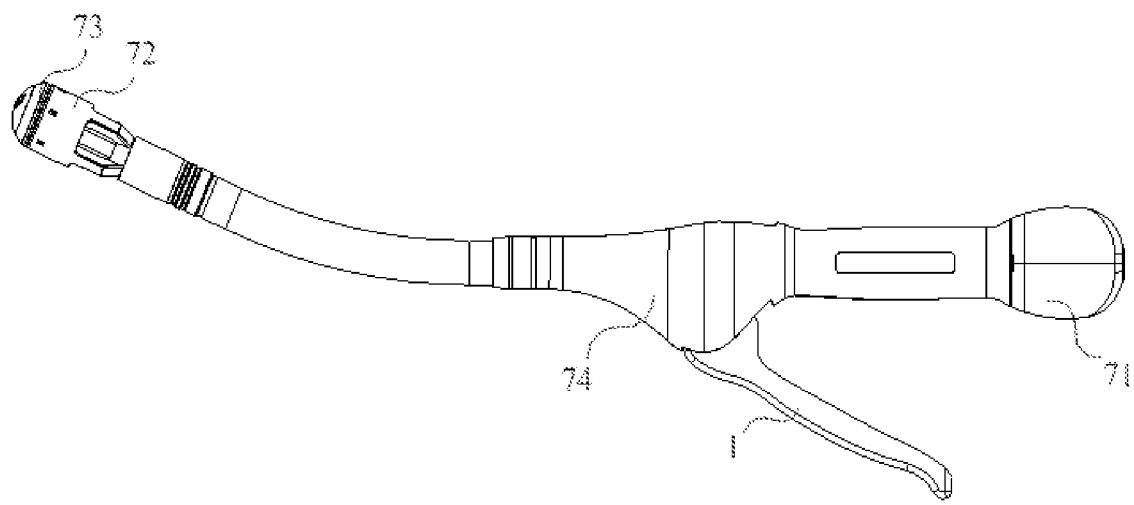
FIG. 1 is a schematic view of a conventional circular stapler according to an embodiment of the present disclosure.
Figure 2:
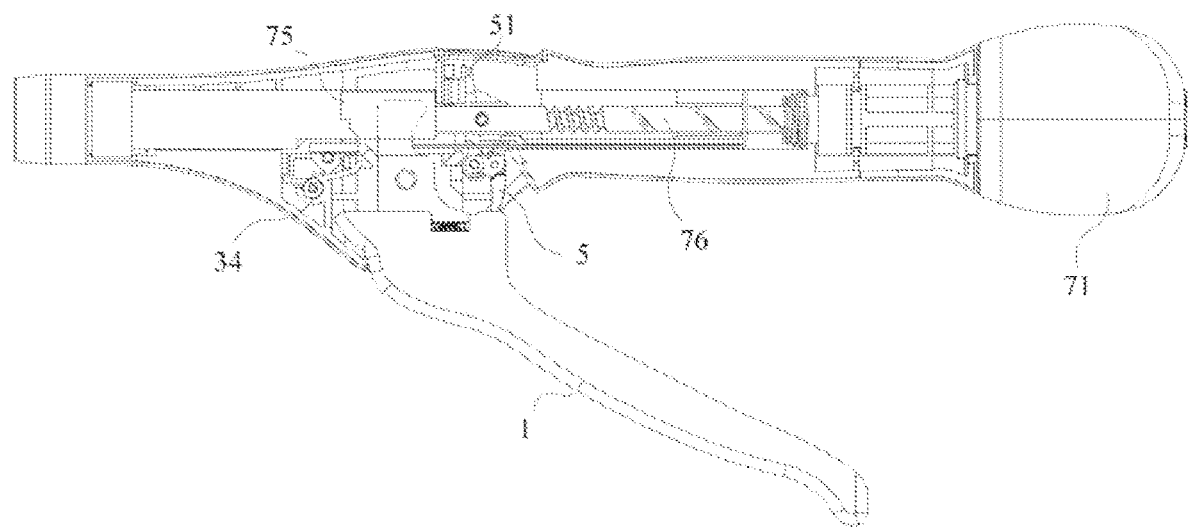
FIG. 2 is a schematic view of a cooperating structure of a conventional stapler and a handle assembly according to an embodiment of the present disclosure.

FIGS. 1 and 2 show a structure of a conventional stapler in an initial state according to an embodiment of the present disclosure. The stapler includes an instrument body, a handle assembly movably connected to the instrument body, and a staple pushing rod 75 disposed in the instrument body. The staple pushing rod 75 has an initial position and a firing position, and the staple pushing rod 75 can be pushed to the firing position, by the handle assembly, from the initial position. In this embodiment, an anvil assembly 73 and a cartridge assembly 72 cooperated with the anvil assembly 73 are disposed on a distal end of the instrument body, and a knob 71 for the operator to hold is disposed at a proximal end of the instrument body. FIGS. 1 and 2 only show an optional structure of the stapler, which should not be regarded as a limitation of the scope of the present disclosure.

When the staple pushing rod 75 moves to the firing position, the staple pushing rod 75 can further push a staple pushing sheet and an annular cutter of the stapler, to suture and cut the tissues being operated. In order to prompt the operator of the firing state of the stapler, the present disclosure further disposes an indicator 5 and a strike part inside the instrument body. The indicator 5 is rotatably connected to the instrument body, and in a not ready-to-fire state and a ready-to-fire state, the first end 51 of the indicator 5 is in the first position area and the second position area, respectively. The first position area includes an initial position where the first end 51 of the indicator 5 is located at in the initial state (i.e., the not ready-to-fire state), and the second position area includes a position where the first end 51 of the indicator 5 is located at in the ready-to-fire state. Wherein, a window is provided on the instrument body corresponding to the first position area and the second position area, and the window is used for observing the position of the first end 51 of the indicator 5 during operation. When the first end 51 of the indicator 5 is in the first position area, the stapler is in an insurance state and cannot be fired; when the first end 51 of the indicator 5 is in the second position area, the stapler can be fired. In order to prompt the doctor more intuitively, an area on the window corresponding to the second position area which indicating the stapler can be fired is colored green, which has been disclosed in the prior art. When the stapler is in the initial state, the first end 51 of the indicator 5 is in the first position area and the indicator 5 is located correspondingly to the strike part. At this time, the indicator 5 can be pressed against the strike part, or there can be a certain gap between the indicator 5 and the strike part. When the stapler is in the firing state, the first end 51 of the indicator 5 is moved to the second position area, and the first end 51 of the indicator 5 is rotated towards the proximal end of the stapler to move away from the strike part. After the stapler being fired, the first end 51 of the indicator 5 returns to the first position area from the second position area, strikes the strike part and emits the strike sound. Through the strike sound, the operator can know that the stapler has been fired.

Figure 3:
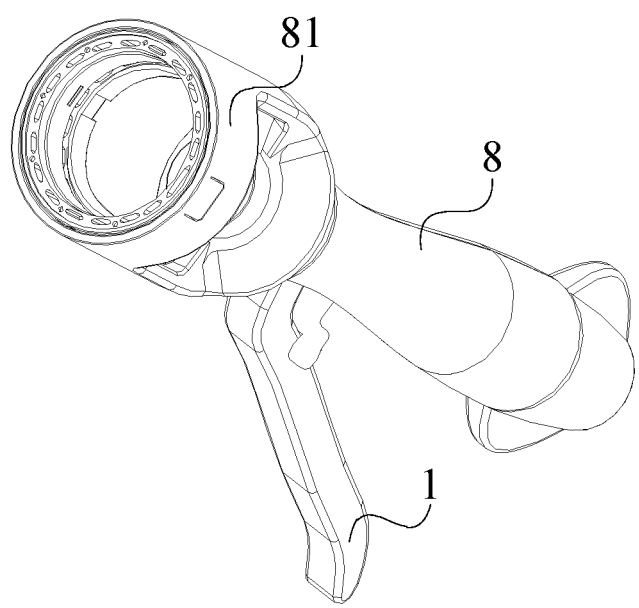
FIG. 3 is a schematic view of a circumcision stapler according to an embodiment of the present disclosure.
Figure 4:
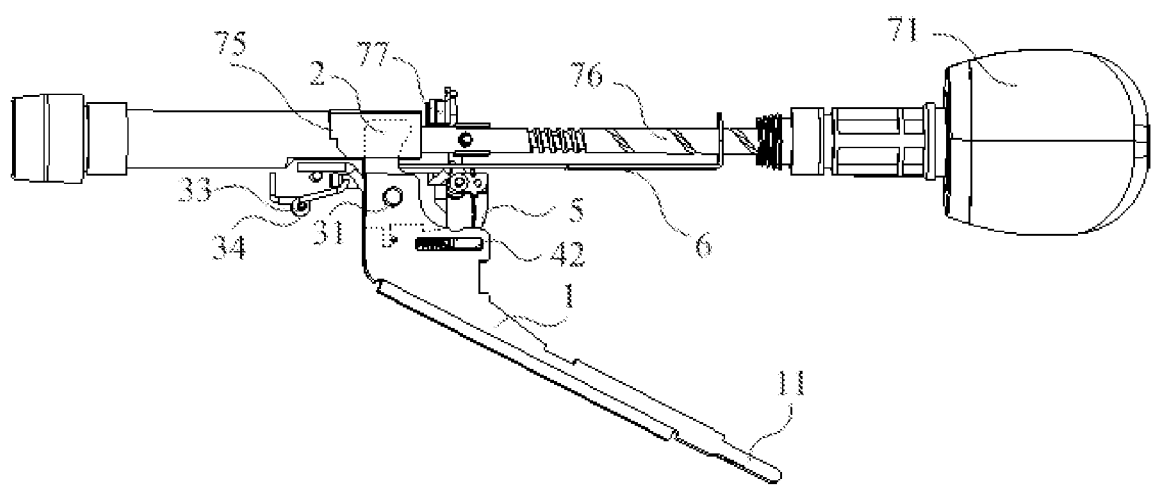
FIG. 4 is a schematic view of a circular stapler in an initial state according to an embodiment of the present disclosure.
Figure 5:
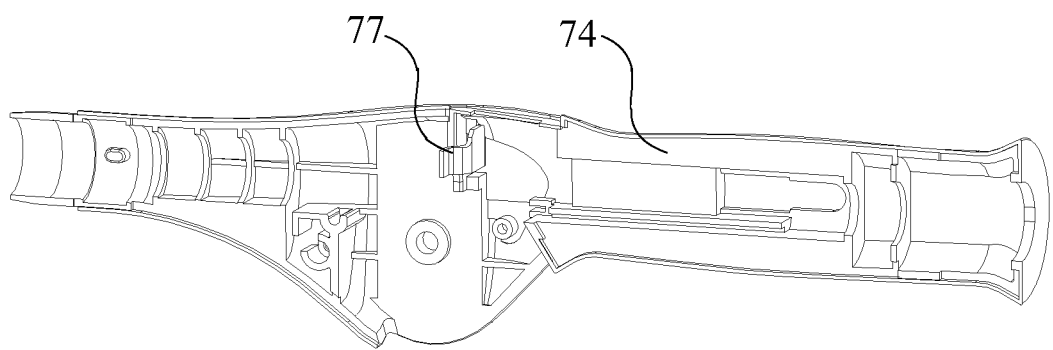
FIGS. 5 and 6 are schematic views of cooperating structures of a stapler casing on one side of the circular stapler and a metal sheet according to an embodiment of the present disclosure.
Figure 6:
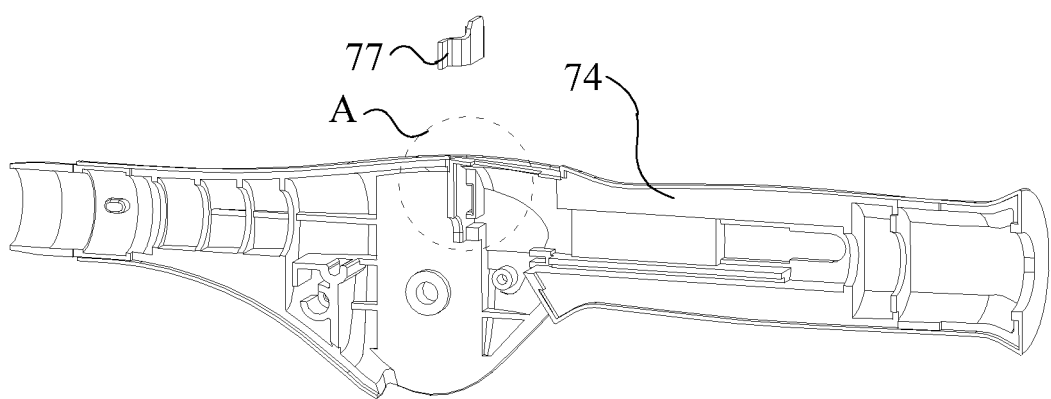

The present disclosure can be applied not only to the conventional circular stapler, but also to a circumcision stapler. For example, FIG. 3 shows a structure of a body portion of the circumcision stapler 8 to which the handle assembly is applied. A cartridge assembly 81 and a glans cap assembly (not shown in FIG. 3) cooperated with the cartridge assembly 81 are disposed at a distal end of the body portion of the circumcision stapler 8. When using the circumcision stapler, the handle assembly is movably connected to one end of the circumcision stapler, and one end of the handle assembly is cooperated with a staple pushing component of the circumcision stapler. When a firing condition is met, the staple pushing component will be pushed by the handle assembly and the circumcision stapler will be fired.

The strike part in this embodiment is a metal sheet 77. Specifically, a structure of the strike part in this embodiment is shown in FIGS. 4 to 8. In this embodiment, the instrument body includes two stapler casings 74 on two sides of the instrument body, respectively, and the cooperating structure of the strike part and the stapler casing 74 on the one side is respectively shown in FIGS. 5 and 6. A first end 771 and a second end 772 of the metal sheet 77 are respectively fixed to inner surfaces of the two stapler casings 74, and a middle portion of the metal sheet 77 is protruded toward the proximal end of the stapler to form a protruding portion 773, so the metal sheet 77 forms a hollow structure. When the indicator 5 strikes the protruding portion 773 of the metal sheet 77, a loud sound can be made and a better prompt effect can be achieved.

Figure 7:
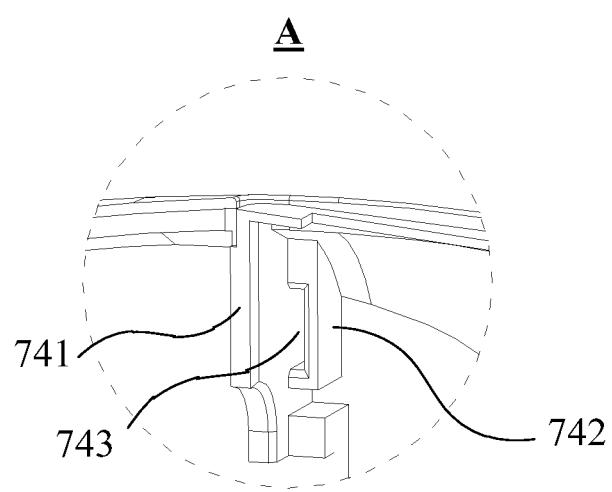
FIG. 7 is an enlarged view of an area A shown in FIG. 6.
Figure 8:
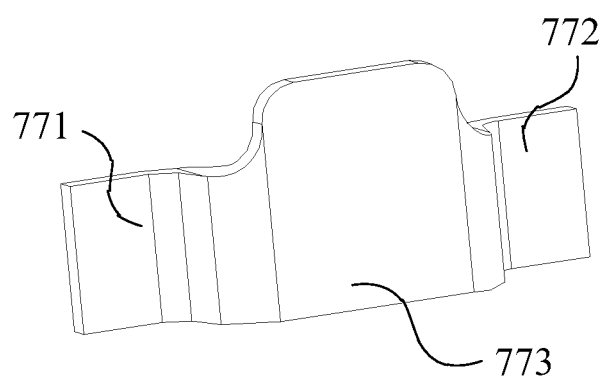
FIG. 8 is a schematic view of the metal sheet according to an embodiment of the present disclosure.
Figure 9:
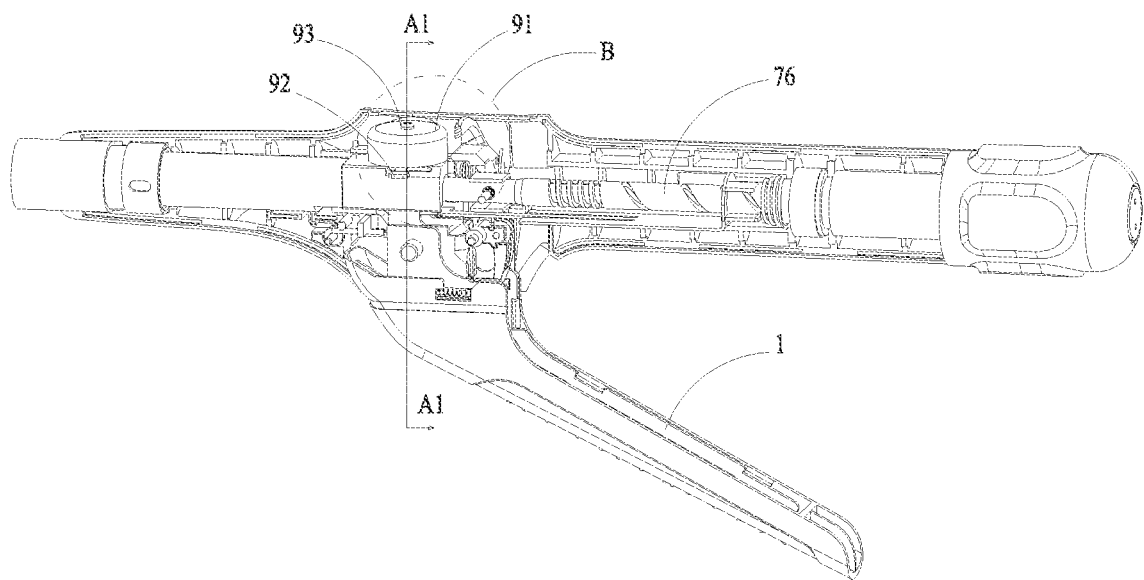
FIG. 9 is a schematic view of the circular stapler in the initial state according to another embodiment of the present disclosure.

As shown in FIG. 7, a rib plate 741 and a fixing plate 742 are disposed on the inner surface of each stapler casing 74, and a fixing slot 743 is formed between the rib plate 741 and the fixing plate 742, the ends 771, 772 of the metal sheet 77 are inserted into two fixing slots 743, respectively. Specifically, the fixing plate 742 can be a bent plate with both sides bent toward the rib plate 741, and after the fixing plate 742 is fixed to the rib plate 741, a cavity between the fixing plate 742 and the rib plate 741 forms the fixing slot 743.

In this embodiment, the strike part can be a metal sheet with a middle portion bent toward the indicator 5, but the present disclosure is not limited to this. In other embodiments, the strike part can be a hollow sphere or a hemisphere with a spherical surface facing the proximal end of the stapler, or the strike part can be made with other materials, such as plastic, acrylic, etc., which fall within the scope of the present disclosure.

In another embodiment of the present disclosure, the strike part is a bell assembly. Specifically, a structure of the bell assembly is shown in FIGS. 9 to 13. In this embodiment, the strike part includes a bell 91 and a bracket 92, and the bell 91 is fixed to the stapler casings 74 through the bracket 92. In the initial state, the first end 51 of the indicator 5 is located correspondingly to the bell 91, and the first end 51 of the indicator 5 can be pressed against the bell 91, or be not in contact with the bell 91 to form a gap between the first end 51 of the indicator 5 and the bell 91. Herein, an elastic limiting member 78 facing a direction of the indicator 5 is disposed on the stapler casing 74, and the first end 51 of the indicator 5 is made not in contact with the bell 91 when in the initial state. When the stapler is being fired, the first end 51 of the indicator 5 is moved to the proximal end of the stapler and away from the bell 91; when the firing of the stapler is completed, the first end 51 of the indicator 5 returns to the first position area from the second position area, strikes the bell 91 and emits the strike sound, which also achieves the effect of prompting the operator that the firing has been completed through the strike sound. As the first end 51 of the indicator 5 can be made not in contact with the bell 91 through the elastic limiting member 78, after the firing is completed, the elastic limiting member 78 will drive the indicator 5 to leave the bell 91 immediately after striking the bell 91, to avoid hindering the vibration of the bell 91, thereby improving the sound tone and sound quality of the bell 91 and extending the duration time of the sound.

Figure 10:
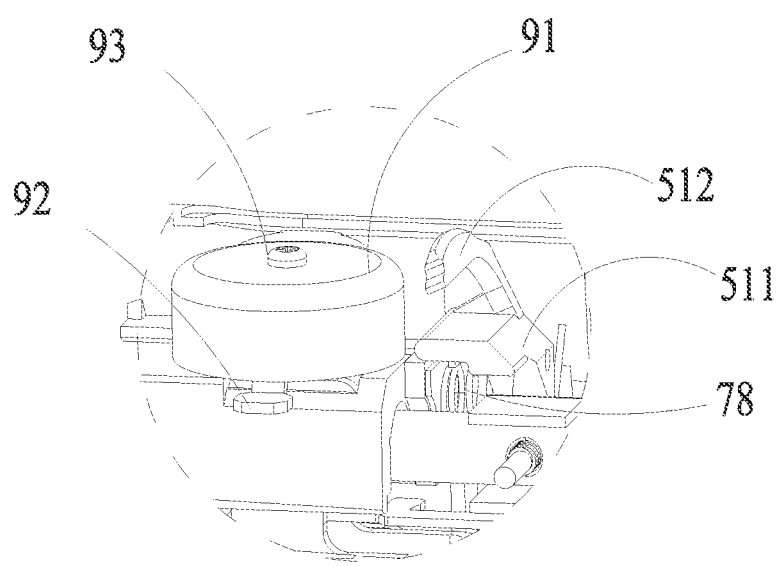
FIG. 10 is an enlarged view of an area B shown in FIG. 9.

As shown in FIG. 10, in this embodiment, the elastic limiting member 78 is a spring, a distal end of the spring is fixed to the stapler casing 74, and a free end of the spring is held against the first end 51 of the indicator 5. Of course, in another alternative embodiment, the spring can be fixed to the first end 51 of the indicator 5 through the proximal end thereof and be held against the stapler casing 74 through the free end thereof.

Figure 11:
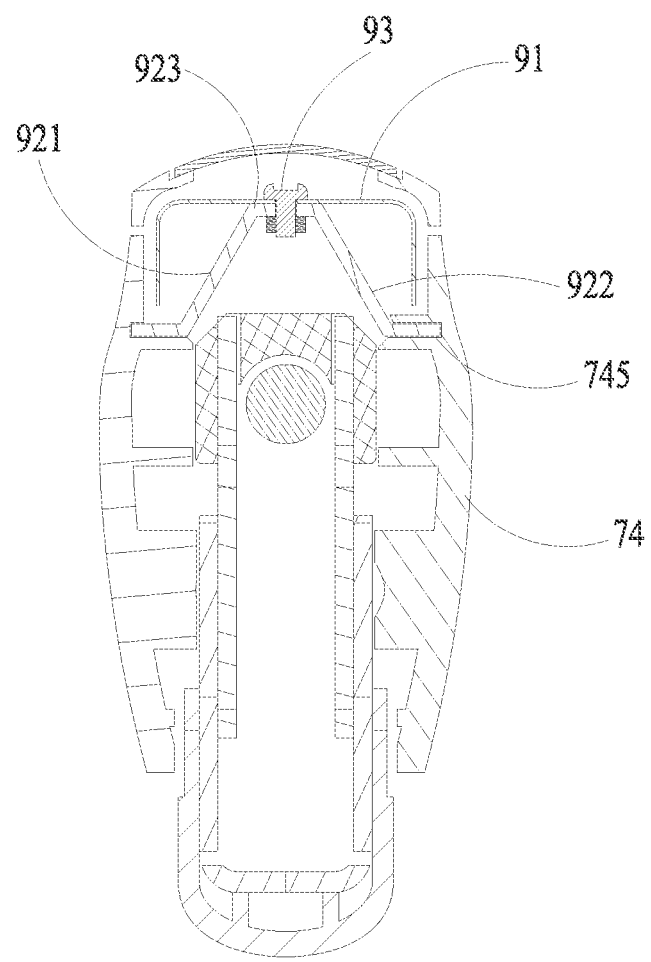
FIG. 11 is a sectional view in an A1-A1 direction shown in FIG. 9.

As shown in FIG. 11, in this embodiment, the instrument body includes two stapler casings 74 on two sides of the instrument body, respectively, and two ends of the bracket 92 are respectively fixed to the stapler casings 74 on the two sides. Specifically, two slots 745 are respectively opened in inner surfaces of the stapler casings 74, and two ends of the bracket 92 are inserted into the two slots 745 on the two sides, respectively.

The bell 91 is a hollow cylinder with an opening in bottom surface. The bracket 92 includes a connecting part 923 and a first side arm 921 and a second side arm 922 on both sides of the connecting part 923. The connecting part 923 of the bracket 92 is fixedly connected to a middle portion of an upper surface of the bell 91, and terminal ends of the first side arm 921 and the second side arm 922 of the bracket 92 are respectively fixed to the stapler casings 74 on the two sides. The connecting part 923 of the bracket 92 and the bell 91 can be connected to each other by bolts, rivets and other fasteners, the bracket 92 can also be directly welded to the bell 91, or by other connecting methods, which fall within the scope of the present disclosure.

Figure 12:
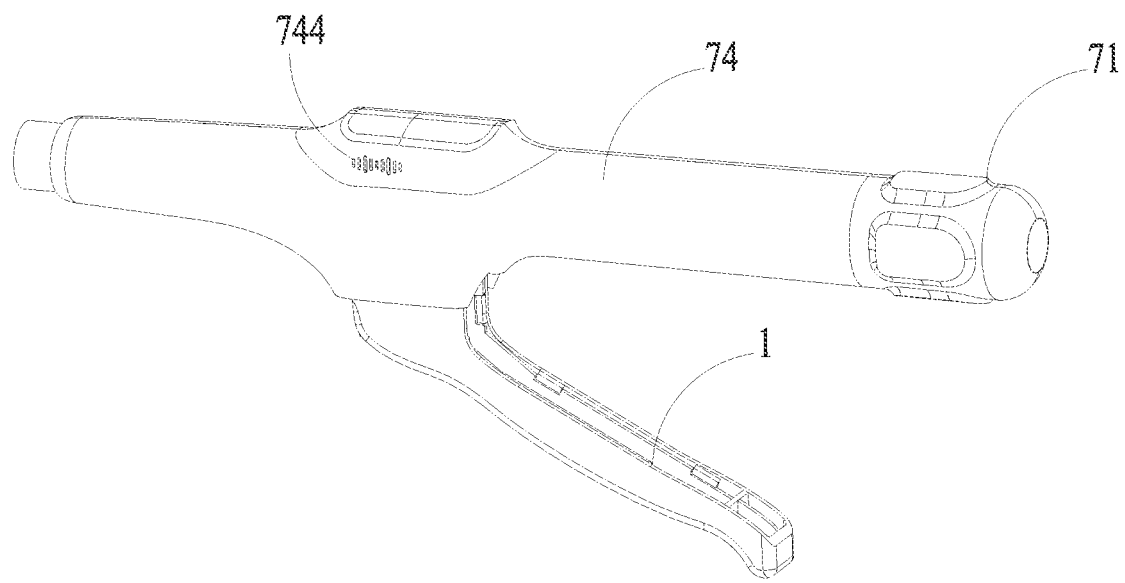
FIG. 12 is a schematic view of an external structure of the circular stapler according to another embodiment of the present disclosure.
Figure 13:
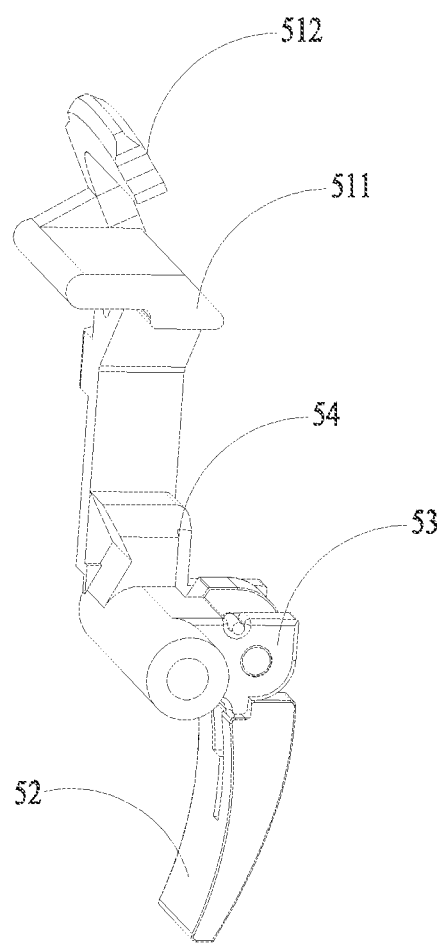
FIG. 13 is a schematic view of an indicator according to another embodiment of the present disclosure.
Figure 14:
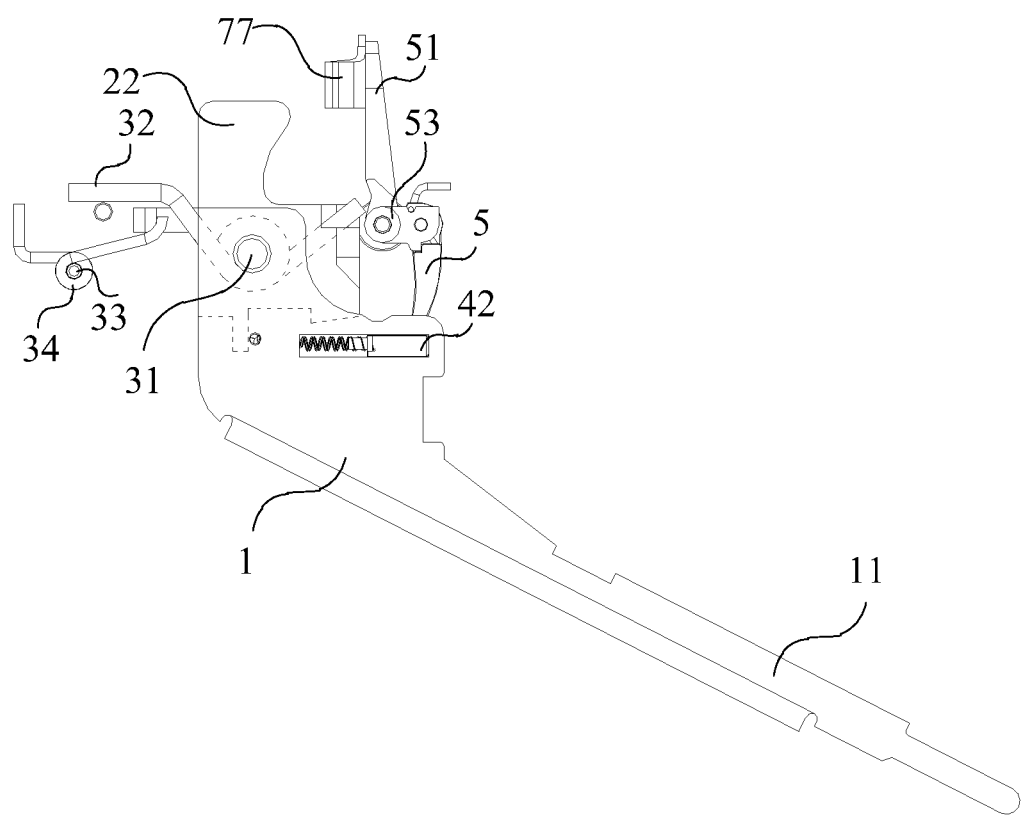
FIGS. 14 and 15 are schematic views of a handle assembly in the initial state, of the circular stapler, according to an embodiment of the present disclosure.

As shown in FIG. 12, there is a sound hole 744 for transmitting the sound opened on the stapler casing 74 on one side, or there are two sound holes 744 opened on the stapler casings 74 on the two sides, respectively. The position of the sound hole 744 corresponds to the bell 91, which will increase the volume of the bell when it is struck.

The structure of the indicator 5 is shown in FIG. 13 to FIG. 18. In this embodiment, the indicator 5 is rotatably fixed to the instrument body through a positioning part 53. A positioning pin 55 passes through the positioning part 53, an indicator return torsion spring 56 is sleeved on the positioning pin 55, and two ends of the indicator return torsion spring 56 are respectively pressed against the indicator 5 and the instrument body. In the initial state and the fired state, the indicator 5 is in a balanced state and maintained in the first position area, under a combined action of the elastic limiting member 78 and the indicator return torsion spring 56. When the first end 51 of the indicator 5 is moved to the second position area under an external force toward the proximal end of the stapler, the indicator return torsion spring 56 is deformed; and when the external force acting on the indicator 5 disappears, a restoring force of the indicator return torsion spring 56 can push the indicator 5 back to the first position area to strike the strike part. During striking, the first end 51 of the indicator 5 needs to overcome the action of the elastic limiting member 78 and move quickly toward the distal end to strike the strike part. The first end 51 of the indicator 5 includes a firing part 511 which protrudes toward the distal end of the stapler to be better matched with the strike part. The first end 51 of the indicator 5 further includes an indicating part 512 which corresponds to the position of the window of the stapler. Therefore, a current position of the first end 51 of the indicator 5 can be determined, by observing the position of the indicating part 512 through the window, and whether the stapler is ready to be fired can be seen by the operator.

Specifically, in the initial state, the firing part 511 at the initial position is not in contact with the bell 91. When the first end 51 of the indicator 5 is moved to the second position area under the external force toward the proximal end of the stapler, the indicator return torsion spring 56 produces a first torsional deformation. After the stapler being fired, the first end 51 of the indicator 5 is free from the external force, and the deformation restoring force of the indicator return torsion spring 56 will drive the first end 51 of the indicator 5 to quickly swing toward the distal end of the stapler. After moving to the initial position, the firing part 511 of the indicator 5 will continue swinging toward the distal end of the stapler for a short distance with a current acceleration, to strike the bell 91. During the short distance of continuing rotating with the current acceleration, the indicator return torsion spring 56 will produce a relatively small second torsional deformation. After the firing part 511 strikes the bell 91, the deformation restoring force of the indicator return torsion spring 56 will pull the firing part 511 back to the initial position, and further, under the action of the elastic limiting member 78, the firing part 511 is quickly separated from the surface of the bell 91 and no longer be in contact with the bell 91, therefore the firing part 511 will not strike the bell 91 again. In this embodiment, the first position area is a range of position including the initial position of the firing part 511, the striking position when the firing part 511 strikes the bell 91, and a position area between the initial position and the striking position. The second position area can also be a range of position, and not necessarily a specific position point. Within the range of the second position area, the stapler can be fired.

Figure 15:
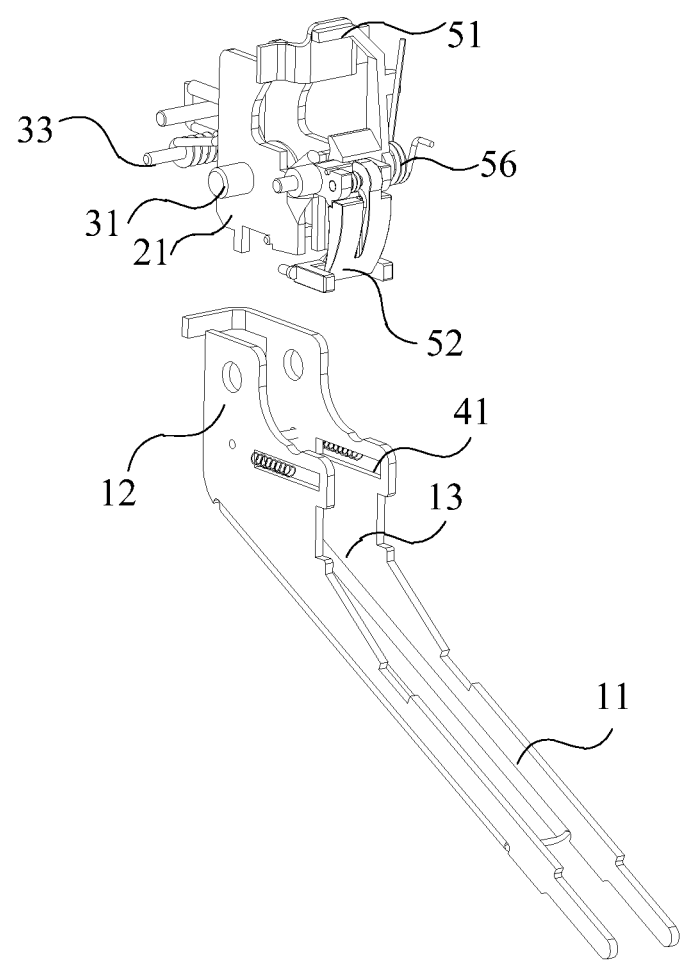
Figure 16:
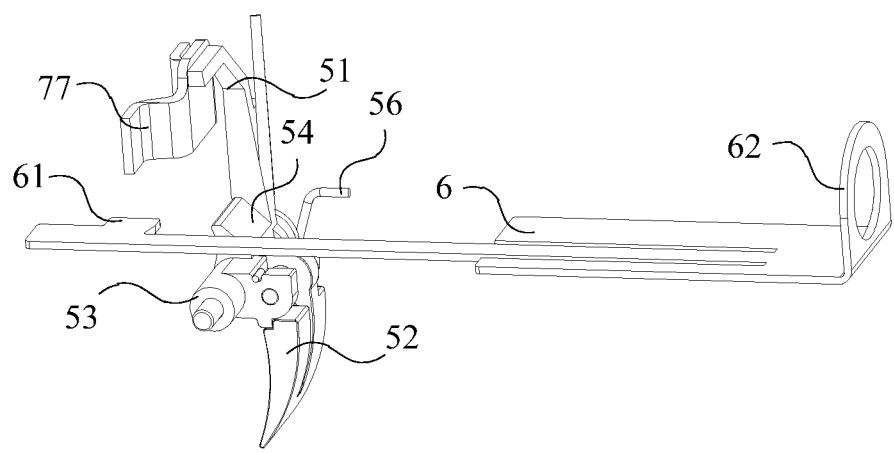
FIG. 16 is a schematic view of a cooperating structure of the indicator in the initial state and a pulling sheet according to an embodiment of the present disclosure.

In other embodiments, the indicator 5 can be provided without the firing part 511, thereby, when the first end 51 of the indicator 5 returns to the first position area from the second position area, the indicating part 512 of the indicator 5 will strike the strike part and emits the strike sound. The structure of this kind of indicator is shown in FIG. 15, wherein the staple pushing rod 75 is located between the first end 51 and the positioning part 53 of the indicator 5, and the indicating part 512 of the indicator 5 protrudes toward a direction of the staple pushing rod 75. FIG. 15 shows that a length of a protruding portion of the indicating part 512 of the indicator 5 is nearly equal to a length of a protruding portion in the middle of the metal sheet 77, which can increase the contact area between the indicator 5 and the metal sheet 77 when striking each other. Further, a structure for avoiding the interference with the staple pushing rod 75 is formed between the indicating part 512 and the positioning part 53 of the indicator 5, which helps to arrange the positions of the indicator 5 and the staple pushing rod 75 inside the instrument body more rationally and flexibly, and reduce the overall thickness of the instrument body, thereby realizing a compact and small structure of the stapler.

Furthermore, a pulling sheet 6 is disposed inside the stapler and a protruding portion 54 is disposed on the indicator 5. When the handle assembly is not rotated and the pulling sheet 6 is moved toward the proximal end of the stapler, the pulling sheet 6 can pull the protruding portion 54 of the indicator 5 and drive the first end 51 of the indicator 5 to move to the second position area from the first position area. In this embodiment, the pulling sheet 6 includes a hook 61 corresponding to the protruding portion 54 and a tail portion 62 fixed on the screw 76. When the screw 76 is rotated in a certain direction, the pulling sheet 6 can be driven to move toward the proximal end of the stapler.

Furthermore, the indicator 5 can control the firing state of the stapler by controlling the working state of the handle assembly. In this embodiment, the handle assembly includes a first handle 1 and a second handle 2. A first end 11 of the first handle 1 is a holding end, and a second end 12 of the first handle 1 is rotatably connected to a first end 21 of the second handle 2. The first handle 1 can be rotated in the first direction under an external force. A second end 22 of the second handle 2 is pressed against the staple pushing rod 75. When the first end 51 of the indicator 5 is in the first position area, the first handle 1 and the second handle 2 are not fixedly linked with each other, and even if the first handle 1 is rotated, the second handle 2 will not push the staple pushing rod 75 to fire the stapler. In this embodiment, the first direction is a counterclockwise direction shown in FIGS. 17 and 20, but the present disclosure is not limited to this. When the doctor presses the first handle 1, the first handle 1 can be easily rotated, while the second handle 2 will not be triggered, at the same time, the force of pressing the first handle 1 is very small since the stapler is in an invalid firing state right now. The doctor can also know through the operation experience that the stapler is currently not fired, and the casing of the stapler will not be cracked.

When the first end 51 of the indicator 5 is in the second position area, the first handle 1 and the second handle 2 are fixedly linked with each other, the rotation of the first handle 1 will drive the rotation of the second handle 2, thereby the staple pushing rod 75 will be pushed to the firing position and the stapler will be fired.

Specifically, the first handle 1 has a first cavity 13, and in the initial state, the second handle 2 is partially located inside the first cavity 13. The first handle 1 is provided with a sliding slot 41 including a first section and a second section connected to each other, and a slider 42 is slidably arranged in the sliding slot 41. The second end 22 of the second handle 2 has a handle contact portion. When the first end 51 of the indicator 5 is in the first position area, the slider 42 is located in the first section of the sliding slot 41; when the first handle 1 is pressed and rotated counterclockwise, the slider 42 is not pressed against the second handle 2 and the second handle 2 continues to enter the first cavity 13 of the first handle 1; when the first end 51 of the indicator 5 is moved to the second position area, the slider 42 will be pushed to the second section of the sliding slot 41 to interfere with the second handle 2, by the second end 52 of the indicator 5, and when the first handle 1 is rotated counterclockwise, the slider 42 is pressed against the handle contact portion of the second handle 2 and pushes the second handle 2 to rotate.

It should be noted that the first section and the second section of the sliding slot 41 in the present disclosure are relative concepts, which not necessarily mean the two ends of the sliding slot 41. In the view shown in FIG. 14, the first section is located on the right side of the second section of the sliding slot 41. When the slider 42 is located in the first section of the sliding slot 41, the slider 42 will not interfere with the second handle 2; and when the slider 42 is located in the second section of the sliding slot 41, it will interfere with the second handle 2.

In this embodiment, there is a first pin 31 passing through the first handle 1 and the second handle 2, simultaneously, and the first pin 31 is fixed to the stapler casing 74 with a first torsion spring 32 sleeved thereon. Both ends of the first torsion spring 32 are respectively pressed against the stapler casing 74 and the second handle 2. After the second handle 2 is rotated, the restoring force of the first torsion spring 32 will reset the second handle 2 in the case that the external force is released. In order to reset the first handle 1, a second pin 33 is disposed inside the stapler casing 74, the second pin 33 is fixed to the stapler casing 74 with a second torsion spring 34 sleeved thereon. Both ends of the second torsion spring 34 are respectively pressed against the stapler casing 74 and the first handle 1.

Only an optional structure of the handle assembly is described here. In practical applications, the handle assembly can adopt other structures, for example, in an alternative embodiment, only one handle is provided without distinguishing a first handle and a second handle, or in another alternative embodiment, the connection method between the first handle and the second handle can be changed, which all fall within the scope of the present disclosure.

Figure 17:
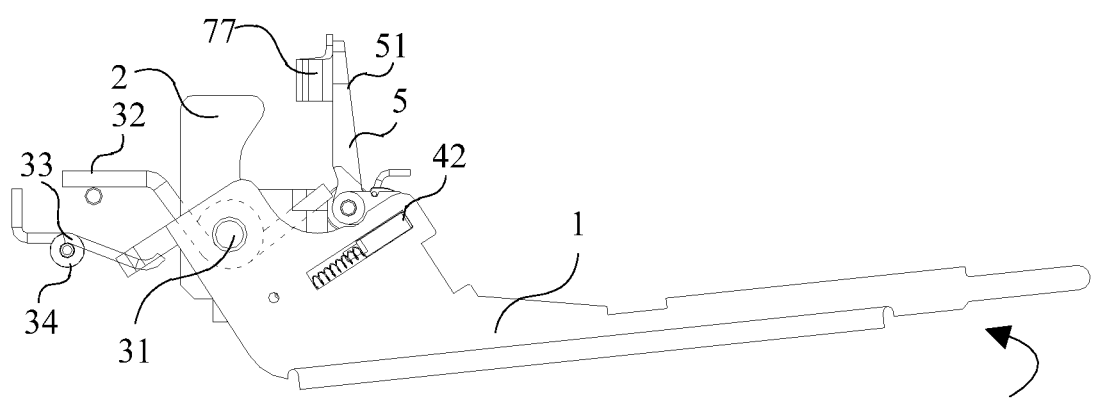
FIG. 17 is a schematic view of the handle assembly in an invalid state, of the circular stapler, according to an embodiment of the present disclosure.
Figure 18:
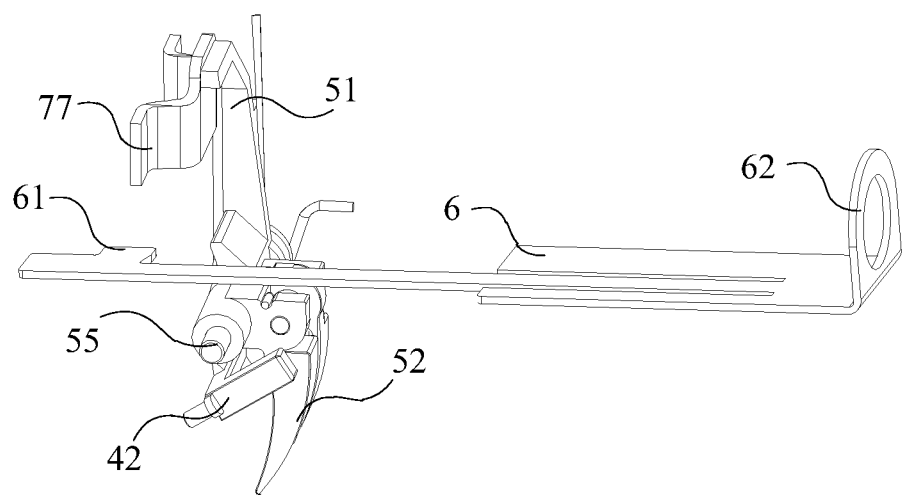
FIG. 18 is a schematic view of a cooperating structure of the indicator in the invalid state and the pulling sheet according to an embodiment of the present disclosure.

FIGS. 17 and 18 show the structure of the stapler in the invalid state of this embodiment. In the invalid state, the indicator 5 is not pulled by the pulling sheet 6, so the position of the indicator 5 is not changed. At this time, the first end 51 of the indicator 5 is located in the first position area and the slider 42 is still located in the first section of the sliding slot 41, thereby, in the rotation path of the first handle 1, the slider 42 will not interfere with the handle contact portion of the second handle 2. It should be noted that in the initial position, under the action of a slider return spring, the slider 42 is located at a terminal end of the first section of the sliding slot 41, i.e., a right end position as shown in FIGS. 17 and 18, away from the second section of the sliding slot 41. Of course, the initial position of the slider 42 can also be limited by the second end 52 of the indicator 5. At this time, the stapler is in an insurance state. Since the torsion force of the second torsion spring 34 is much smaller than the firing force, the first handle 1 can be rotated counterclockwise around the first pin 31 when receives a small holding force from the operator, and the second handle 2 can continue to enter the cavity 13 of the first handle 1, that is, the first handle 1 and the second handle 2 are not fixedly linked with each other and the second handle 2 is not rotated. When the operator presses the first handle 1, the first handle 1 can be easily rotated while the second handle 2 is not driven to rotate, so the stapler cannot be fired. The operator can also get a tactile feedback at this time, knowing that the first end 51 of the indicator 5 has currently not reached the second position area and the stapler has not been fired. When the external force is released, the first handle 1 will be reset under the action of the second torsion spring 34.

It can be seen from FIG. 18, since the indicator 5 does not actually move, the first end 51 of the indicator 5 is still in contact with the strike part. The slider 42 moves with the rotation of the first handle 1, and a relative position between the slider 42 and the second end 52 of the indicator 5 is changed.

Figure 19:
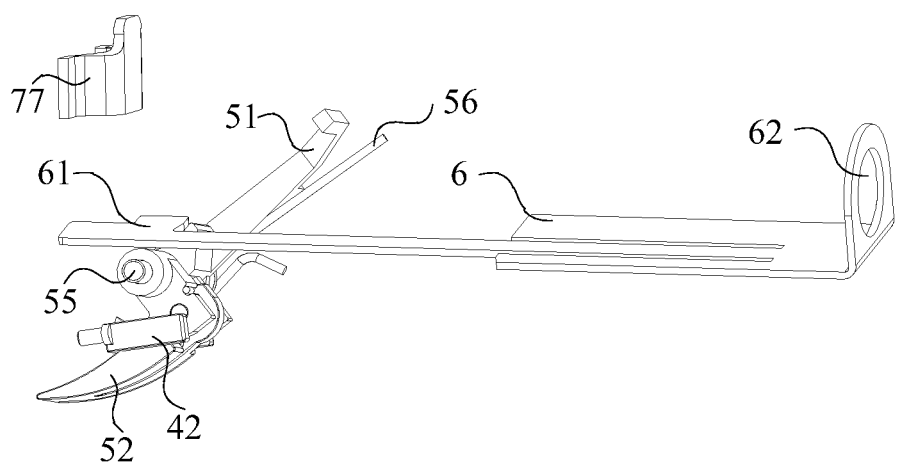
FIG. 19 is a schematic view of the pulling sheet pulling the indicator to rotate according to an embodiment of the present disclosure.

As shown in FIG. 19, when the operator prepares to fire the stapler, the operator can rotate the knob 71 to drive the screw 76 to rotate, thereby driving the pulling sheet 6 to move toward the proximal end of the stapler. The hook 61 of the pulling sheet 6 is pressed against the protruding portion 54 of the indicator 5 and pulls the indicator 5 to rotate clockwise, therefore, the first end 51 of the indicator 5 enters the second position area from the first position area.

Figure 20:
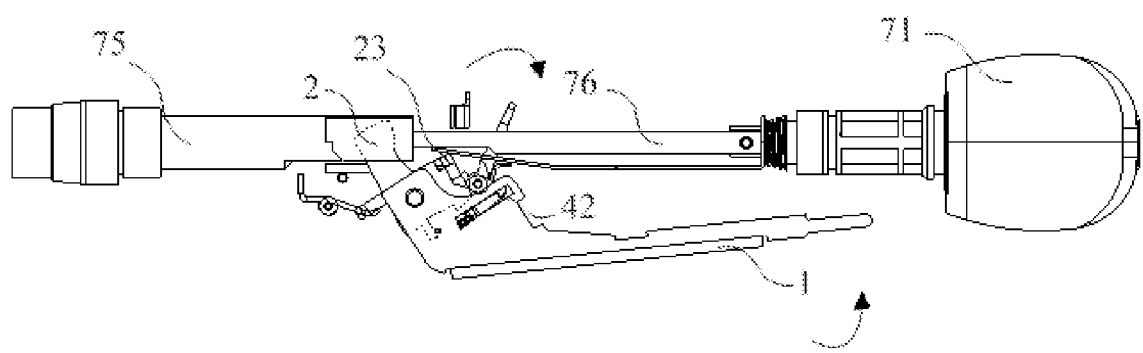
FIG. 20 is a schematic view of the circular stapler in a firing state according to an embodiment of the present disclosure.

FIG. 20 shows a structure of the stapler in the firing state of this embodiment. During the firing process, the second end 52 of the indicator 5 is rotated clockwise, and the slider 42 is pushed to move to the second section of the sliding slot 41. When the operator presses the first handle 1, the first handle 1 is rotated counterclockwise, and the slider 42 is pressed against the handle contact portion and prevents the second handle 2 from continuing entering the internal cavity 13 of the first handle 1. As a result, the second handle 2 and the first handle 1 become fixedly linked with each other, thereby the second handle 2 is rotated counterclockwise with the first handle 1, and the second end 22 of the second handle 2 pushes the staple pushing rod 75 to move toward the distal end of the stapler to complete the firing of the stapler.

Figure 21:
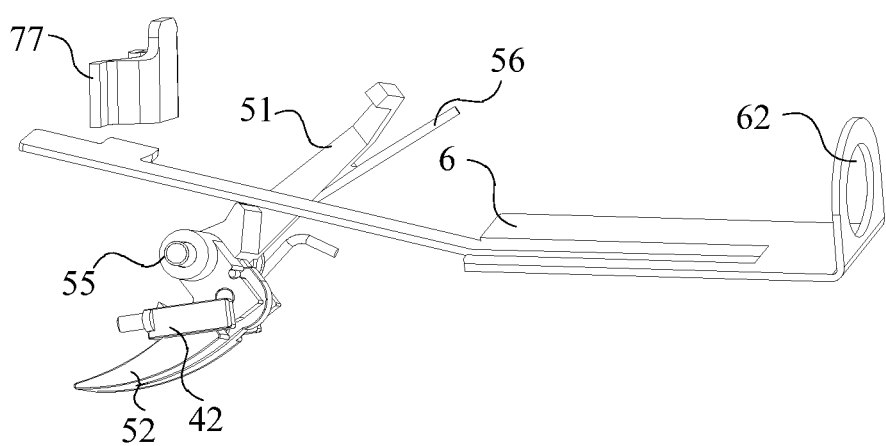
FIG. 21 is a schematic view of the pulling sheet being pushed up according to an embodiment of the present disclosure.

As shown in FIG. 20, during the firing process, a pulling sheet contact portion 23 of the second handle 2 will be pressed against the pulling sheet 6 and push up the pulling sheet 6, thereby the pulling sheet 6 is separated from the protruding portion 54 of the indicator 5 and a state shown in FIG. 21 is formed. After the firing is completed, since the pulling sheet 6 no longer pulls the indicator 5, the first end 51 of the indicator 5 will return to the first position area under the restoring force of the indicator return torsion spring 56, strike the strike part and emit the strike sound, which prompts the operator that the firing has been successfully completed.

Hearing the strike sound, the operator can determine that the stapler has been fired and then release the first handle 1. The second end 52 of the indicator 5 will be separated from the slider 42 after the first handle 1 is released, since the first end 51 of the indicator 5 has returned to the first position area. Then, after the slider return spring is free from the external force of the indicator 5, the deformation force of the slider return spring when it returns to its original state will push the slider 42 to slide again to the first section of the sliding slot 41 to return to its initial position. The second handle 2 is also reset under the restoring force of the first torsion spring 32. Since the first handle 1 is engaged with the second handle 2 under the action of the slider 42, the first handle 1 will be reset with the second handle 2 and at the same time be reset under the action of the second torsion spring 34.

The circular stapler provided by the present disclosure has following advantages.

The present disclosure provides a circular stapler with the strike part disposed inside the instrument body. When firing the stapler, the first end of the indicator is moved to the second position area from the first position area, and away from the strike part; when the firing is completed, the first end of the indicator returns to the first position area from the second position area, strikes the strike part and emits the strike sound. The strike sound prompts the operator that the firing has been successfully completed, so that the operator can know the firing state of the stapler in time and the user experience of the operator can be improved.

The above is a detailed description of the present disclosure in connection with the specific preferred embodiments, and the specific embodiments of the present disclosure are not limited to the description. Modifications and substitutions can be made without departing from the spirit and scope of the present disclosure.

What is claimed is:

1. A circular stapler comprising:
an instrument body;
a handle assembly movably connected to the instrument body; and
a staple pushing rod disposed in the instrument body, wherein the staple pushing rod has an initial position and a firing position, and the staple pushing rod is capable of being pushed to the firing position, by the handle assembly, from the initial position;
characterized in that, the circular stapler further comprising:
an indicator, a strike part and a pulling sheet disposed in the instrument body, wherein the indicator is rotatably connected to the instrument body and provided with a protruding portion, and the handle assembly is provided with a pulling sheet contact portion;
when the circular stapler is in an initial state, a first end of the indicator is in a first position area and located correspondingly to the strike part; when the circular stapler is in a firing state, the pulling sheet pulls the protruding portion and drives the first end of the indicator to move to a second position area and away from the strike part; as the firing state progresses, pushed up by the pulling sheet contact portion, the pulling sheet is separated from the protruding portion, then after the circular stapler being fired, the first end of the indicator returns to the first position area from the second position area, strikes the strike part and emits a strike sound.

2. The circular stapler of claim 1, wherein an elastic limiting member is disposed in the instrument body, and a free end of the elastic limiting member is oriented toward and held against the first end of the indicator, when located in the first position area, the first end of the indicator is not held against the strike part.

3. The circular stapler of claim 2, wherein the elastic limiting member is a spring.

4. The circular stapler of claim 2, wherein the indicator further comprises a positioning part, and the indicator is rotatably fixed to the instrument body through the positioning part.

5. The circular stapler of claim 4, wherein a firing part protruding toward a distal end of the circular stapler is disposed on the first end of the indicator; after the stapler being fired, the indicator returns to the first position area from the second position area, and the firing part of the indicator strikes the strike part and emits the strike sound.

6. The circular stapler of claim 4, wherein the circular stapler further comprises a positioning pin passing through the positioning part, and an indicator return torsion spring is sleeved on the positioning pin.

7. The circular stapler of claim 4, wherein the instrument body comprises two stapler casings disposed on two sides of the instrument body, respectively, the positioning part is fixed to the stapler casing on one side, and the first end of the indicator comprises an indicating part protruding toward the stapler casing on the other side.

8. The circular stapler of claim 1, wherein the first end of the indicator is connected to a distal end of the pulling sheet.

9. The circular stapler of claim 1, wherein the instrument body comprises two stapler casings disposed on both sides of the circular stapler, respectively, a first end and a second end of the strike part are respectively fixed to inner surfaces of the two stapler casings, and a middle portion of the strike part is protruded toward a proximal direction of the circular stapler.

10. The circular stapler of claim 9, wherein a rib plate and a fixing plate are disposed on the inner surface of each of the stapler casings, and a fixing slot is formed between the rib plate and the fixing plate, both ends of the strike part are respectively inserted into two fixing slots.

11. The circular stapler of claim 1, wherein the strike part is a metal sheet with a middle portion bent toward a proximal direction of the circular stapler.

12. The circular stapler of claim 1, wherein the strike part is a hollow sphere or a hemisphere with a spherical surface facing a proximal direction of the circular stapler.

13. The circular stapler of claim 1, wherein the strike part comprises a bell and a bracket, and the bell is fixed to the instrument body through the bracket.

14. The circular stapler of claim 13, wherein the instrument body comprises two stapler casings disposed on two sides of the instrument body, respectively, and two ends of the bracket are respectively fixed to the stapler casings on the two sides.

15. The circular stapler of claim 14, wherein an inner surface of each of the stapler casings is provided with a slot, and the two ends of the bracket are respectively inserted into slots on the two sides.

16. The circular stapler of claim 14, wherein the bell is a hollow cylinder with an opening on a bottom surface, and the bracket comprises a connecting part and a first side arm and a second side arm disposed on both sides of the connecting part, the connecting part of the bracket is fixedly connected to a middle portion of an upper surface of the bell, and terminal ends of the first side arm and the second side arm of the bracket are respectively fixed to the stapler casings on the two sides.

17. The circular stapler of claim 1, wherein the instrument body comprises a stapler casing, and at least one sound hole is opened at a position, of the stapler casing, corresponding to the strike part.

* * * * *